(12) United States Patent  (10) Patent No.: US 8,308,715 B2
Farnan et al.  (45) Date of Patent: Nov. 13, 2012

(54) CANNULA STABILIZER

(75) Inventors: Robert C. Farnan, Rivervale, NJ (US);
Oliver Marseille, Aachen (DE)

(73) Assignee: Circulite, Inc., Saddle Brook, NJ (US)

( * ) Notice: Subject to any disclaimer, the term of this patent is extended or adjusted under 35 U.S.C. 154(b) by 0 days.

(21) Appl. No.: 12/917,525

(22) Filed: Nov. 2, 2010

(65) Prior Publication Data

US 2011/0118668 A1  May 19, 2011

Related U.S. Application Data

(60) Provisional application No. 61/261,029, filed on Nov. 13, 2009.

(51) Int. Cl.
*A61B 17/00* (2006.01)
*A61B 17/08* (2006.01)

(52) U.S. Cl. .......................... 606/1; 606/151

(58) Field of Classification Search .......... 604/172–175; 607/126; 606/151–158, 1
See application file for complete search history.

(56) References Cited

U.S. PATENT DOCUMENTS

| | | | |
|---|---|---|---|
| 5,073,169 A * | 12/1991 | Raiken ........................ | 604/180 |
| 5,300,107 A * | 4/1994 | Stokes et al. ................ | 607/126 |
| 5,843,088 A | 12/1998 | Barra et al. | |
| 6,565,536 B1 | 5/2003 | Sohn | |
| 6,585,756 B1 | 7/2003 | Strecker | |
| 6,740,101 B2 | 5/2004 | Houser et al. | |
| 6,843,795 B1 | 1/2005 | Houser et al. | |
| 6,979,338 B1 | 12/2005 | Loshakove et al. | |
| 6,994,713 B2 | 2/2006 | Berg et al. | |
| 7,022,131 B1 | 4/2006 | Derowe et al. | |
| 7,063,711 B1 | 6/2006 | Loshakove et al. | |
| 7,094,248 B2 | 8/2006 | Bachinski et al. | |
| 7,317,951 B2 | 1/2008 | Schneider et al. | |

(Continued)

FOREIGN PATENT DOCUMENTS

WO  2004082742 A1  9/2004

(Continued)

OTHER PUBLICATIONS

U.S. Patent and Trademark Office, International Search Report and Written Opinion in PCT Application No. PCT/US10/055800, Jan. 10, 2011, 8 pages.

(Continued)

*Primary Examiner* — Matthew F DeSanto
(74) *Attorney, Agent, or Firm* — Wood, Herron & Evans, L.L.P.

(57) ABSTRACT

An apparatus and method for stabilizing a cannula to a vascular structure. The stabilizer includes a ring that circumferentially surrounds the cannula. Three or more struts extend distally from the ring and are outwardly-deflected by a first angle relative to a first axis that is parallel to a lengthwise central axis of the cannula. Each strut includes a contact pad that radially extends from the strut and is distally-deflected by a second angle relative to a second axis that is orthogonal to the first axis. Three or more arms extend proximally from the ring and each arm opposes one of the struts. The arms are inwardly-deflected by a third angle relative to the first axis. The stabilizer is configured to move relative to the cannula until the contact pads engage the vascular structure, causing the arms to engage and resist further movement of the stabilizer relative to the cannula.

19 Claims, 8 Drawing Sheets

U.S. PATENT DOCUMENTS

| | | |
|---|---|---|
| 7,340,288 B1 | 3/2008 | Karicherla et al. |
| 2003/0093104 A1 | 5/2003 | Bonner et al. |
| 2004/0024435 A1 | 2/2004 | Leckrone et al. |
| 2005/0065589 A1* | 3/2005 | Schneider et al. ............ 607/126 |
| 2005/0288604 A1* | 12/2005 | Eigler et al. .................. 600/561 |
| 2006/0094983 A1 | 5/2006 | Burbank et al. |
| 2006/0184088 A1 | 8/2006 | Van Bibber et al. |
| 2006/0235357 A1 | 10/2006 | Woodward et al. |
| 2007/0179512 A1* | 8/2007 | Olsen et al. ................... 606/151 |
| 2008/0294189 A1* | 11/2008 | Moll et al. .................... 606/200 |

FOREIGN PATENT DOCUMENTS

| | | |
|---|---|---|
| WO | 2005037345 A2 | 4/2005 |

OTHER PUBLICATIONS

U.S. Patent and Trademark Office, International Preliminary Report on Patentability in corresponding PCT Application No. PCT/US10/55800 mailed Nov. 14, 2011, 5 pp.

* cited by examiner

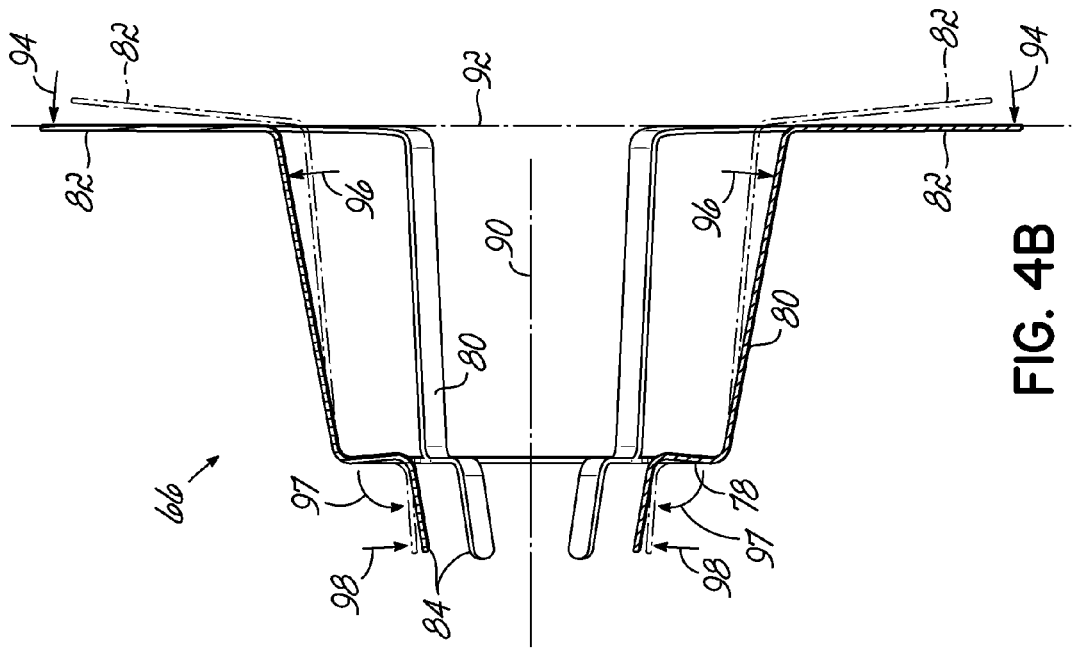
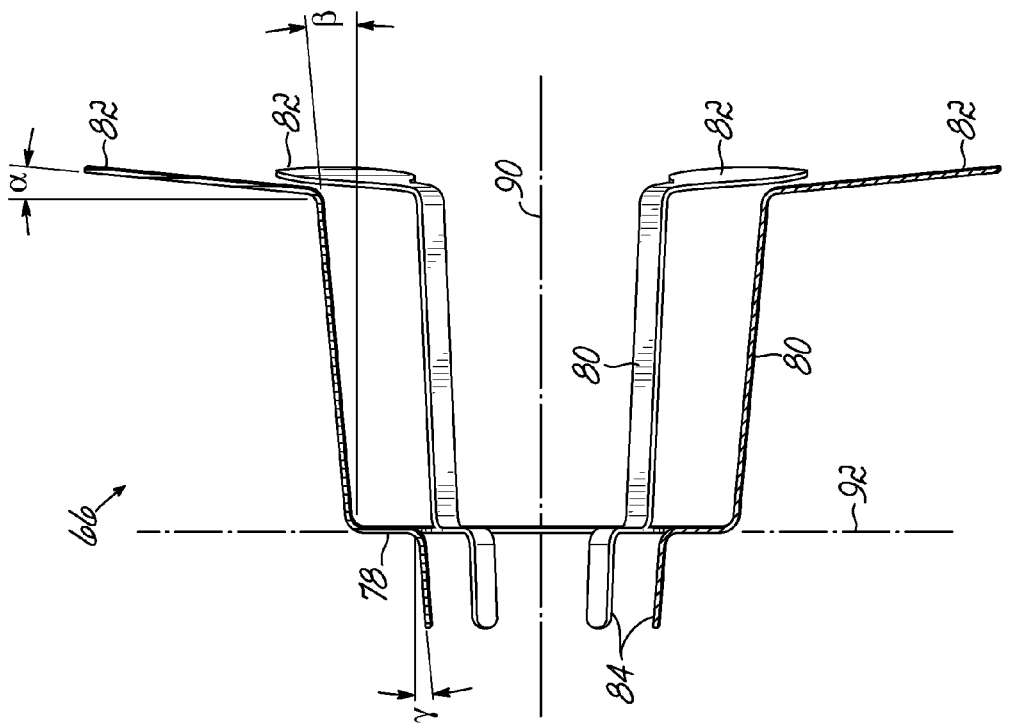

CANNULA STABILIZER

CROSS-REFERENCE TO RELATED APPLICATION

This application claims the priority of U.S. Provisional Patent Application Ser. No. 61/261,029, filed on Nov. 13, 2009, the disclosure of which is incorporated by reference herein.

TECHNICAL FIELD

The invention relates generally to devices and methods for maintaining a fluidic access to the vascular network. More specifically, the invention relates to devices and methods for stabilizing cannulae to the vasculature of a patient.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and into the left ventricle. Finally, the blood is pumped from the left ventricle into the aorta and the vascular network.

Various devices and methods have been utilized to assist the heart in blood circulation, particularly for patients having congestive heart failure (commonly referred to as heart disease), which is a condition that results in any structural or functional cardiac disorder that impairs the ability of the heart to fill with or pump blood throughout the body. These devices generally include a pump, which can reside in a subcutaneous pump pocket, and cannulae fluidically attaching the pump to the vascular network. One cannula can be used to transmit oxygenated blood from a chamber of the heart to the pump; another cannula can be used to direct that blood from the pump to the arterial network.

It is imperative that the distal end of the cannula be stabilized with respect to the vascular structure, i.e., a tip on the distal end should not tilt away from a position that is approximately orthogonal to the wall of the vascular structure. Tilting of the distal end of the cannula can lead to localized stress on the tissue of the vascular structure and possibly a flow obstruction at the tip. While sutures used to synch the tissue surrounding the cannula are somewhat effective in creating hemostasis at the cannula insertion site and to prevent removal of the tip of the cannula, sutures alone do not prevent the movement of the tip from the orthogonal position. There continues to be a need to provide better stabilization of the cannula, particularly the tip, relative to the vascular structure by maintaining the cannula in the more orthogonal position.

SUMMARY

In one illustrative embodiment of the present invention, an apparatus for stabilizing a cannula to a vascular structure is described, i.e., a stabilizer. The stabilizer includes a ring that circumferentially surrounds the cannula. Three or more struts extend distally from the ring and each are outwardly deflected by a first angle relative to a first axis that is parallel to a lengthwise central axis of the cannula. Each strut includes a contact pad that radially extends from the strut and is distally deflected by a second angle relative to a second axis that is orthogonal to the first axis. Three or more arms extend proximally from the ring and each arm opposes one of the struts. The arms are inwardly deflected by a third angle relative to the first axis. The stabilizer is configured to move relative to the cannula until the contact pads engage a wall of the vascular structure causing the arms to engage and resist further movement of the stabilizer relative to the cannula.

In another illustrative embodiment, a method of securing the cannula to the vascular structure with the stabilizer is described. The stabilizer is advanced over the length of the cannula to the wall of the vascular structure. The advancing is continued until the contact pads engage the wall, thereby causing the three or more arms to engage the cannula and resist further movement of the stabilizer.

BRIEF DESCRIPTION OF THE DRAWINGS

FIGS. 4A and 4B are side-elevational views of the stabilizer in a resting position, shown in phantom, and a deflected position, shown in solid.

DETAILED DESCRIPTION

Figure 1:
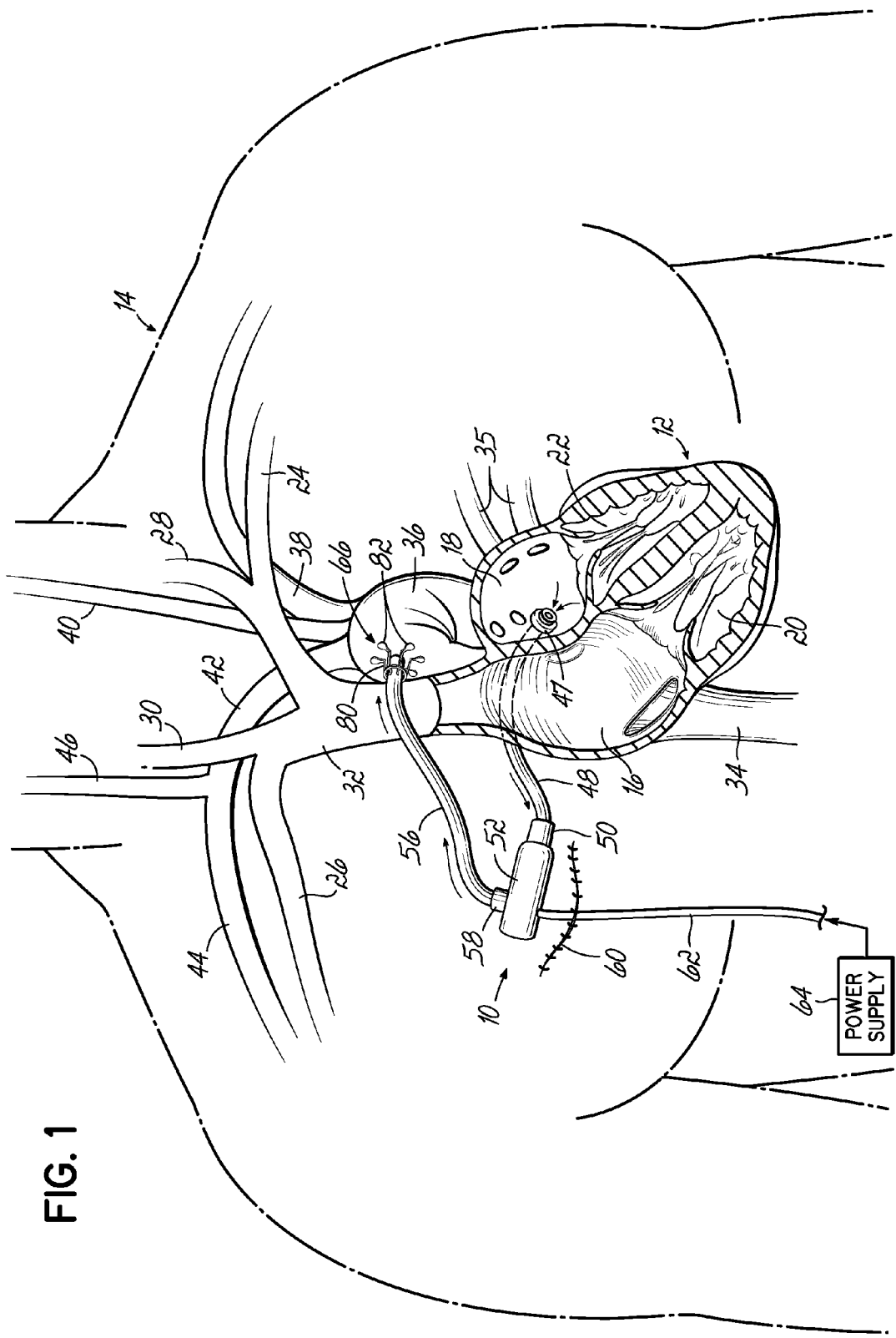
FIG. 1 is a diagrammatic view of a circulatory assist system with an outflow cannula directed from a pump to the aorta and secured with a stabilizer, shown in partial cross-section.

FIG. 1 illustrates an implanted circulatory assist system 10. For illustrative purposes, certain anatomy is shown including the heart 12 of a patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 of the heart 12 from the pulmonary veins 35 and is then pumped into the left ventricle 22. Blood leaving the left ventricle 22 enters the aorta 36 and flows into the left subclavian artery 38, the left common carotid 40, and the brachiocephalic trunk 42 to the right subclavian artery 44 and the right common carotid 46.

With respect to the implanted circulatory assist system 10, a distal end 47 of a flexible cannula body 48 is surgically implanted in the left atrium 18 and extends to an input port 50 of an implantable pump 52. An outflow cannula 56 connects an output port 58 of the implantable pump 52 to an appropriate artery, illustrated here as the aorta 36. The physician may position the implantable pump 52 subcutaneously and, optionally, submuscularly in a pump pocket 60 located near a surgical access site or maintain the pump 52 externally.

A cable 62 can extend transdermally from the pump 52 to a position in the abdomen where the cable 62 exits the patient 14 and connects with a power supply 64. The power supply 64 may be any universal-type power supply that sends power to the pump 52 via the cable 62. For example, the power supply 64 may include rechargeable batteries.

Figure 1A:
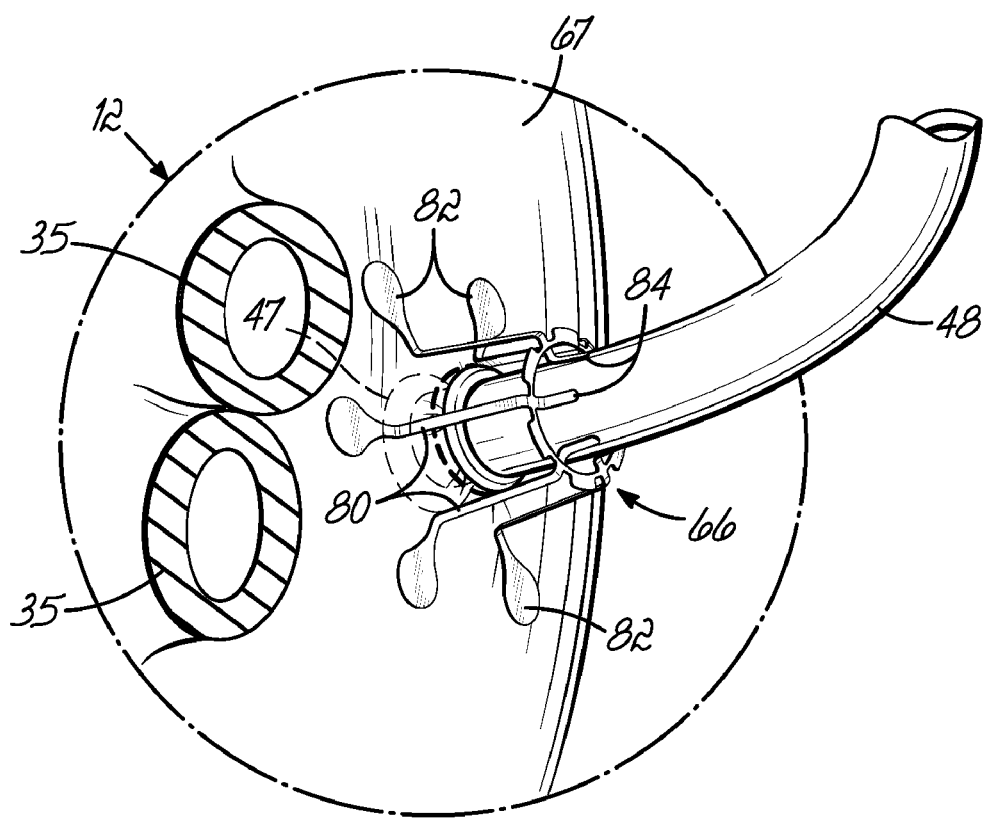
FIG. 1A is an enlarged view of the heart with an inflow cannula directed from the pump to the left atrium and secured to the left atrial wall with the stabilizer.

FIG. 1 illustrates a stabilizer 66 used to secure the outflow cannula 56 to the aorta 36. FIG. 1A illustrates use of the stabilizer 66 with the inflow cannula 48 at an outer wall 67 of the left atrium 18. While only two illustrative uses of the stabilizer 66 are specifically shown, it would be understood that the stabilizer 66 may be used to stabilize a cannula to nearly any vascular structure having sufficient outer surface area.

Figure 2:
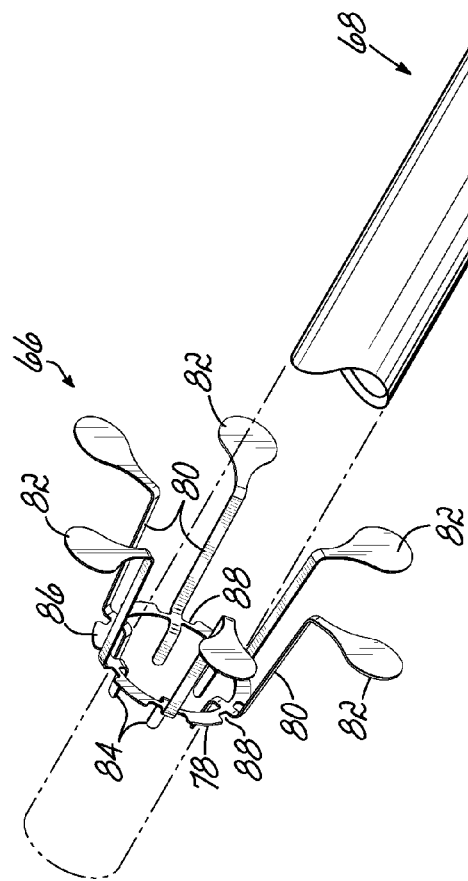
FIG. 2 is a disassembled view of a cannula having a distal tip and the stabilizer.

FIG. 2 illustrates the details of the stabilizer 66 with respect to a generalized cannula 68. The cannula 68 may be any suitable cannula device, such as those constructed from an extruded aliphatic, polycarbonate base polyurethane; aliphatic polyether polyurethane; aromatic polyether polyurethane; aromatic polycarbonate based polyurethane; silicone modified polyurethane; or silicone. Antimicrobial agents may be embedded within the cannula material prior to the forming process to effectively reduce or eliminate the presence of bio-film and reduce the potential for infection. Alternatively, the antimicrobial agent may be applied to the surface of the cannula material after the molding process is complete.

The proximal end (not shown) of the cannula 68 may include a hub (not shown) that aids in coupling the cannula 68 to the implantable pump 52 (FIG. 1) or other auxiliary device. The distal end 47 of the cannula 68 may include a tip 70. In one embodiment, a body 72 of the tip 70 may be constructed from a pliable and/or resilient material, such as a surgical grade silicone or any other suitable biocompatible material. A distal end 74 of the body 72 can be formed such that it will reduce fluidic drag. The tip 70 can be affixed to the cannula 68 by glue, epoxy, or welding.

The tip 70 further includes an anchor 76 that is operable to contact the inner wall surface of a vascular structure. In the illustrated embodiment, the anchor 76 has a disc-like configuration and is a unitary construction with the body 72, such as those that have been taught in U.S. Patent Appl. No. 60/982,322, the disclosure of which is incorporated herein by reference in its entirety. Other configurations for the anchor 76 are known and may be affixed to the body 72, such as those illustrated in U.S. Patent Application Ser. No. 60/823,971, the disclosure of which is also incorporated herein by reference in its entirety.

The stabilizer 66 generally includes a ring 78, three or more struts 80 extending proximally from the ring 78 each having a distally-positioned contact pad 82 extending radially therefrom, and three or more arms 84 extending proximally from the ring 78 each directly opposing one of the three or more struts 80. The stabilizer 66 may be constructed from a sheet of superelastic material, such as nickel-titanium, having a thickness that ranges from about 0.10 mm (0.004 inches) to about 0.36 mm (0.014 inches). The structural pattern is initially cut from the sheet using lasers or a chemical/photo etching process. The pattern is then exposed to secondary bending processes to form the shape of the stabilizer 66. Once appropriately shaped, the stabilizer 66 is then electro-polished to remove any sharp edges and polished to a desired finish, which may be a mirror finish.

While the specific illustrative embodiments shown herein all include six struts 80 and six arms 84, it would be understood that the number of struts 80 and arms 84 may vary and is limited only by the method of manufacture and the amount of material available. The ring 78 is dimensioned to have an inner diameter that is sufficient to receive the outer diameter of the cannula 68 and to freely move relative thereto.

Figure 3:
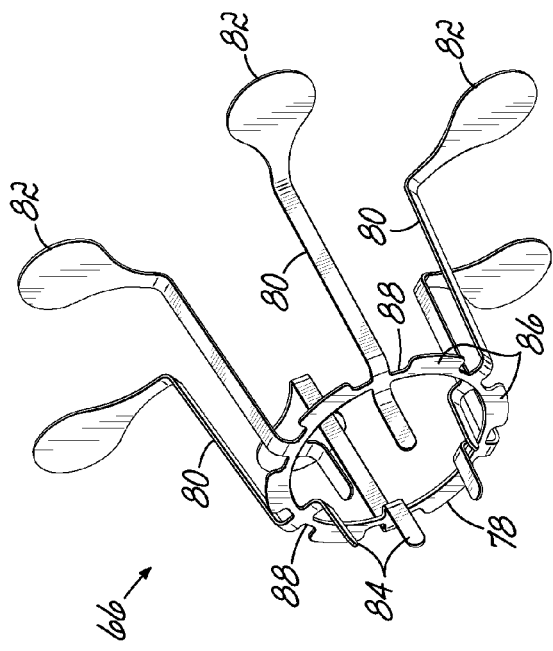
FIG. 3 is a perspective view of the stabilizer.

FIG. 3 illustrates the stabilizer 66 with yet greater detail. Each of the struts 80 may have a cross-sectional area that results in a desired strength and stiffness of the stabilizer 66. Generally the length will be determined by the distance desired to support the cannula 68 in the orthogonal position relative to the lengthwise central axis at the wall of a vascular structure. Lengths may range from about 1 mm (0.04 inches) to about 5 cm (1.97 inches), but should not be so limited. The width of the struts 80 may then be selected to provide the desired strength based on a width-to-thickness ratio. Typically this ratio should be greater than 2:1.

The contact pads 82 may be contoured to minimize trauma and perforation to the wall of the vascular structure. Appropriate contours can include any shape that increases the surface area of the contact pad 82 and that removes sharp edges, e.g., circular, elliptical, or rectangular. As shown, the contact pads 82 each have a width that is greater than the width of its respective strut 80. In some embodiments, the contact pads 82 may further include a porous polymeric material to encourage tissue in-growth and further secure the stabilizer 66 to the tissue. It would be understood that the struts 80 and contact pads 82 need not be uniform in shape or size. That is, it is possible to include struts 80 of varying cross-sectional area or lengths in order to accommodate a particular local anatomy as explained in detail below.

The arms 84 extend distally from the ring 78 and oppose each of the struts 80. When constructed as a unitary structure, the dimensions of the arms 84 are limited to a length of ½ of the inside diameter of the ring 78 and the widths are adjusted according to a desired strength. It would be understood that as the number of arms 84 increases, the length of each arm 84 will decrease because of the maximum circumference of the inside diameter of the ring 78. The lengths of the arms 84 may be extended by welding additional material to the ends of each arm 84 to increase the interference between the arms 84 and the cannula 68, as explained below.

In some embodiments, and as shown in FIG. 3, manipulation tabs 86 may extend radially from the ring 78 and provide a surface for the physician to use in moving the stabilizer 66 relative to the cannula 68. Generally, the number of manipulation tabs 86 will equal the number of struts 80, and accordingly, each of the manipulation tabs 86 will be spaced between two successive struts 80. The manipulation tab width may vary from about 0.5 mm (0.02 inches) to about 10 mm (0.4 inches) and depends on the amount of material that is needed to facilitate the movement of the stabilizer 66, the number of struts 80, and the distance between successive struts 80.

The area where the struts 80 extend from the ring 78 experiences considerable stress during a deflection of the struts 80. To prevent fracture in this area, strain relief grooves 88 may be included to allow for the deflection of the struts 80 and to compensate for additional movements of the vascular structure.

Turning now to FIG. 4A where further detail of the stabilizer 66 can be seen. Specifically, there are at least three angles for proper function of the stabilizer 66. For illustrative purposes only, a first axis 90 is defined as being parallel to a length-wise central axis of the cannula 68 (FIG. 2), and a second axis 92 is defined as being orthogonal to the first axis 90. It would be understood that other frames of reference or coordinate systems could also be used in defining the relative angles.

The first angle, a pad pre-load angle indicated as α in FIG. 4A, is the distally deflected angle of each of the contact pads 82 with respect to the second axis 92. The pad pre-load angle can range from about 1° to about 15° and provides a first moment arm at the radius between the contact pad 82 and the corresponding strut 80 that forces the strut 80 towards the cannula 68 (FIG. 2).

The second angle, a strut angle indicated as β in FIG. 4A, is the outwardly-deflected angle of each of the struts 80 with respect to the first axis 90. The strut angle can range from about 1° to about 15° and provides a second moment arm at the radius between the strut 80 and the ring 78 that forces the ring 78 to locally "twist" towards the cannula 68 (FIG. 2) and in the direction of the arms 84.

The third angle, an arm engagement angle indicated as γ in FIG. 4A, is the inwardly-deflected angle of each of the arms 84 with respect to the first axis 90. The arm engagement angle can vary from about 1° to about 25° where the larger angles cause greater interference with the external surface of the cannula 68 (FIG. 2).

FIG. 4B illustrates the transference of a force applied to the contact pads 82, indicated by arrows 94, to the arms 84 for securing the stabilizer 66 to the cannula 68 (FIG. 2). The stabilizer 66 in a resting position is illustrated in phantom. With the application of the force, the contact pads 82 are deflected from their rest position to a position that generally decreases α. In some embodiments, α may then be less than or equal to 0°. The force is transferred, as indicated with arrows 96, in a manner that generally increases the angle β and creates the localized twist, indicated by moment arm arrows 97 of the ring 78. Finally, the arms 84 are deflected by a force indicated by arrows 98, in a manner that increases γ. It is this increase in γ that causes the arms 84 to engage the cannula 68 (FIG. 2), secures the position of the stabilizer 66, and prevents movement of the stabilizer 66 relative to the cannula 68. Prior to this deflection of the arms 84, the stabilizer 66 may freely move, either proximally or distally, with respect to the cannula 68.

Figure 5A:
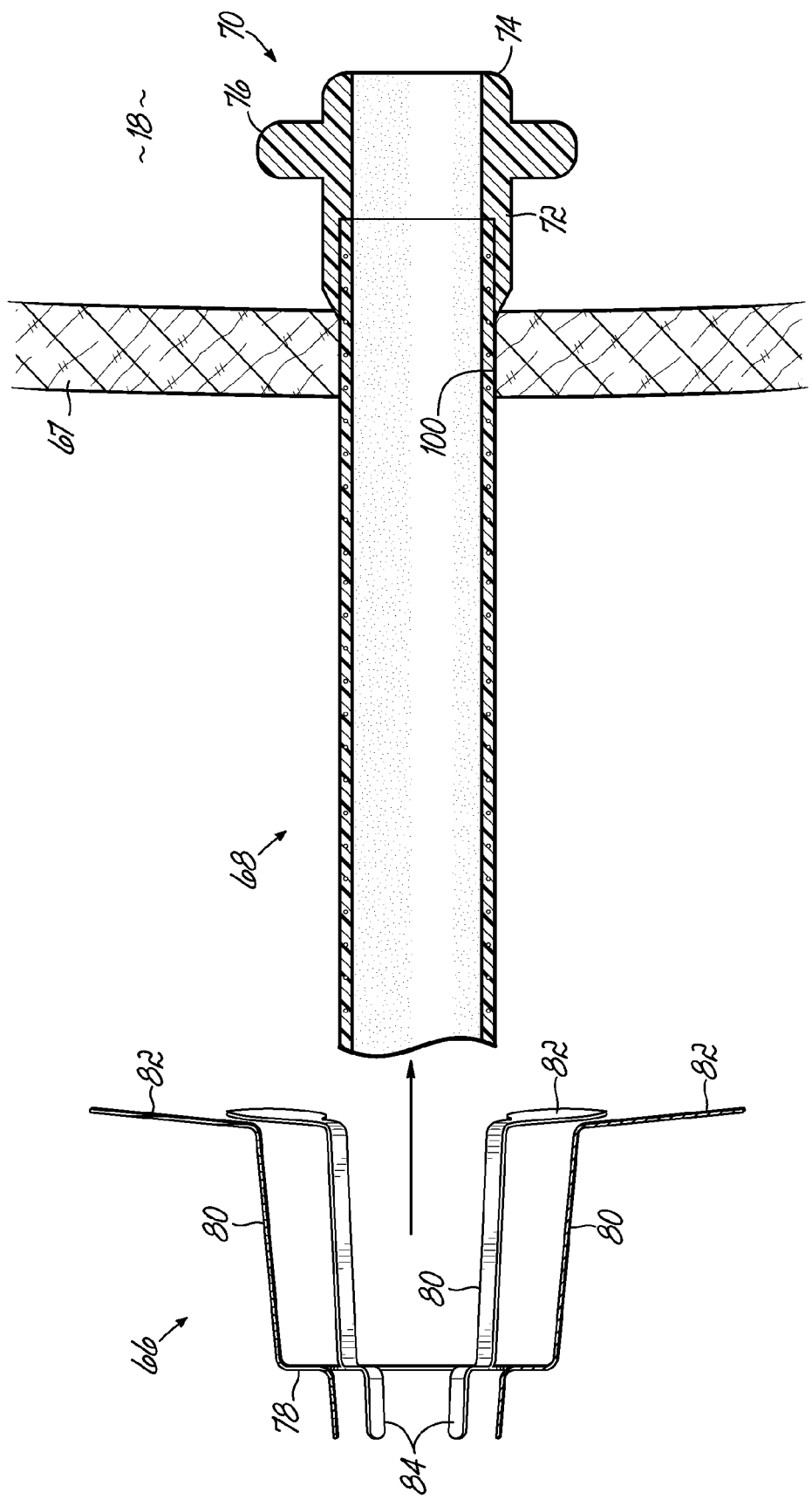
FIGS. 5A-5C are side-elevational views, in cross-section, illustrating successive steps of one exemplary procedure for directing the cannula into the wall of a vascular structure, securing the cannula with purse string sutures, and stabilizing the position of the cannula with the stabilizer.
Figure 5B:
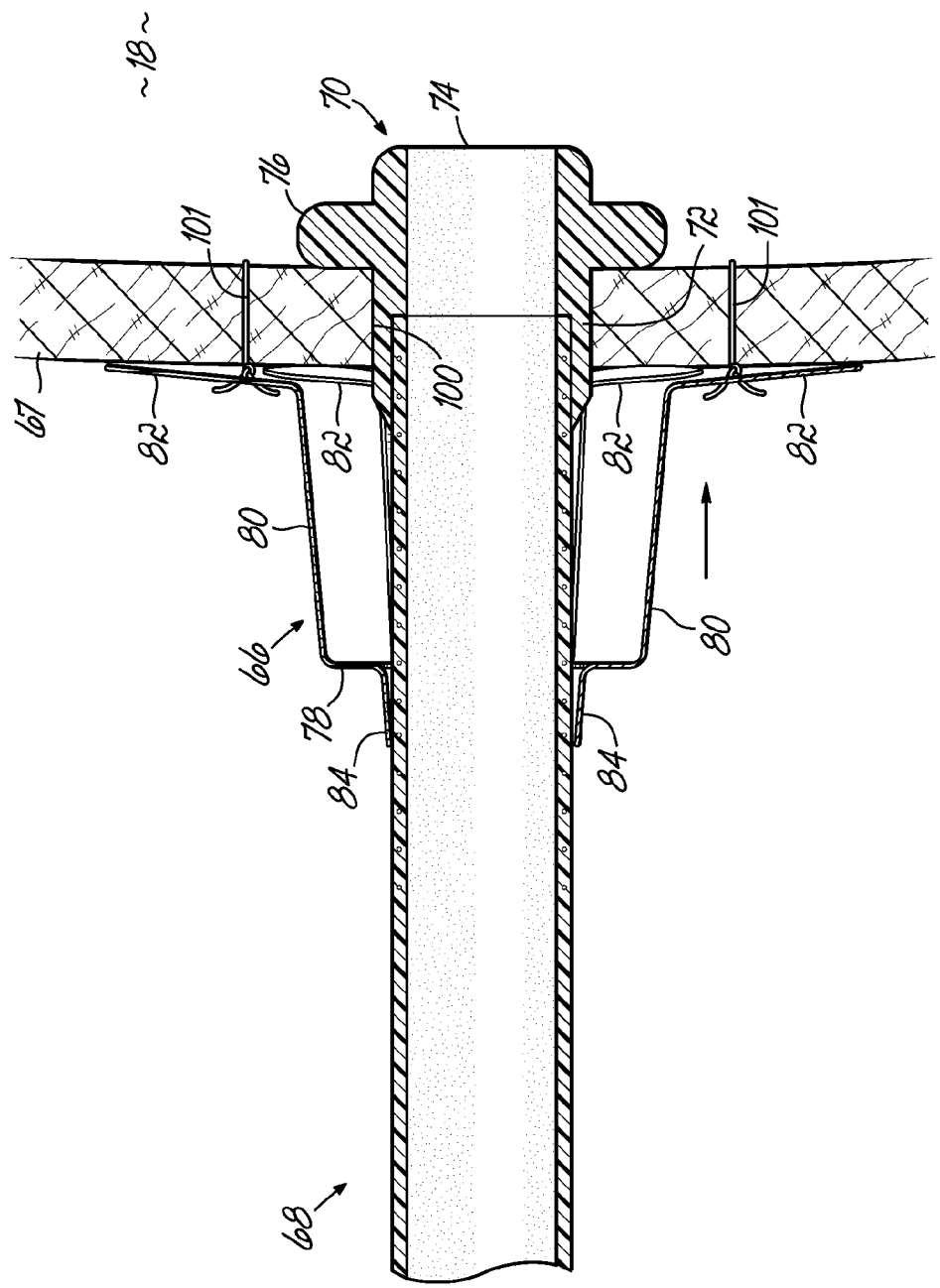
Figure 5C:
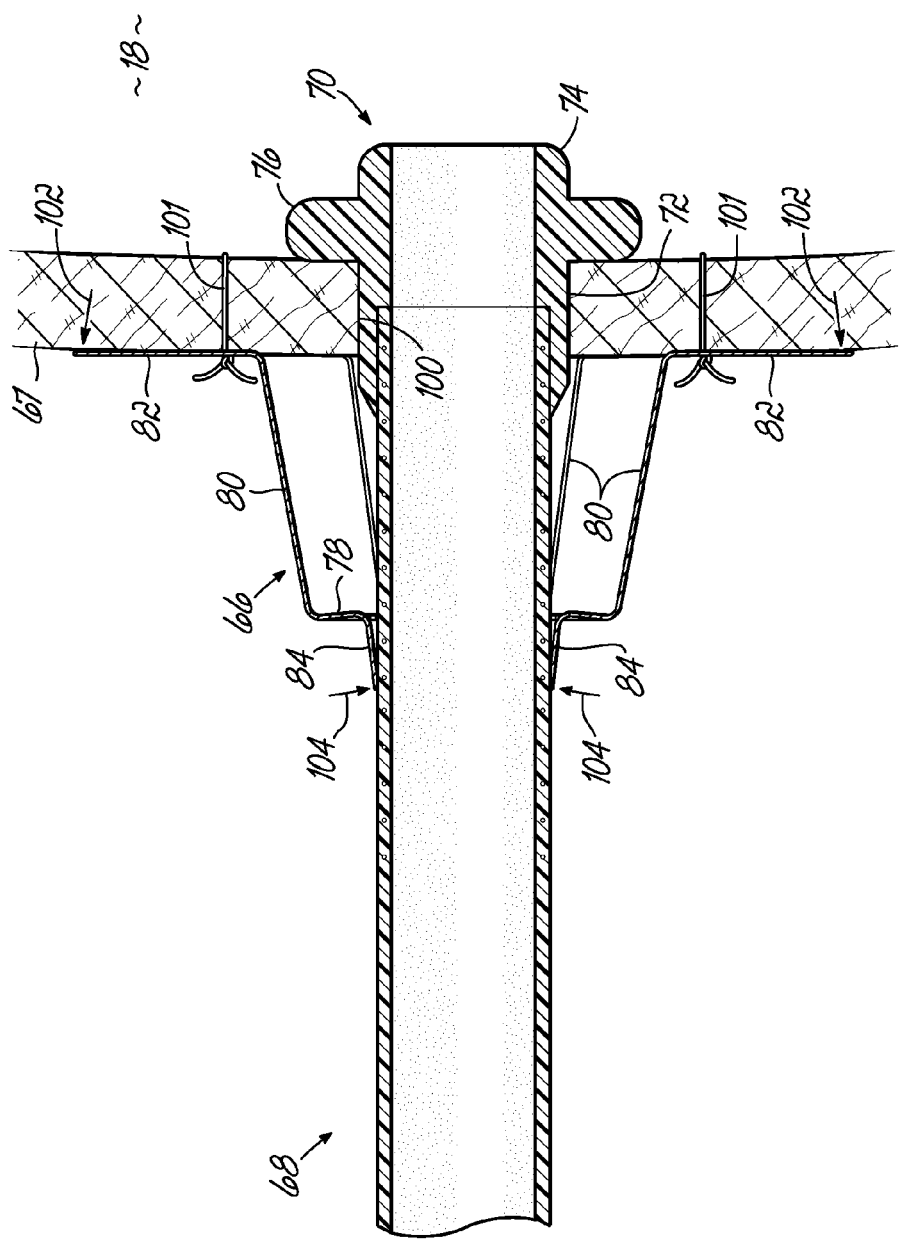

FIGS. 5A-5C illustrate one manner of using the stabilizer 66 in securing the cannula 68 to the wall of a vascular structure, illustrated here as the wall 67 of the left atrium 18; however, it would be understood that the illustrative method could be used to secure the stabilizer 66 to the wall of various vascular structures including arteries and veins.

FIG. 5A illustrates an incision 100 in the wall 67 such that the tip 70 with the anchor 76 of the cannula 68 may be directed into the volume of the left atrium 18. The stabilizer 66 is back-loaded over the proximal end (not shown) of the cannula 68 and advanced over the length of the cannula 68. Alternatively, the stabilizer 66 may be previously preloaded onto the cannula 68, particularly when the cannula 68 includes a proximal hub (not shown) with an outer diameter that is larger than the inner diameter of the ring 78 of the stabilizer 66.

FIG. 5B illustrates the retraction of the cannula 68 such that the proximal surface of the anchor 76 engages the inner surface of the wall 67 within the volume of the left atrium 18. Purse strings 101 are then used to secure the cannula 68 to the wall 67 in a manner that is generally known to one that is skilled in the art. The stabilizer 66 is then advanced further along the cannula 68 until the contact pads 82 make a slight contact with the outer surface of the wall 67.

FIG. 5C illustrates yet continued advancement of the stabilizer 66, until the contact pads 82 fully engage onto the outer surface of the wall 67. The resistance provided by the wall 67, indicated by arrows 102, decreases the pad pre-load angle, α, as was described with reference to FIG. 4B. This force is transferred and creates the twisting of the ring 78 such that the arms 84 are deflected into the soft polymeric material of the cannula 68, which is indicated by arrows 104. The stabilizer 66 is accordingly secured to the cannula 68. However, it would be understood that until the stabilizer 66 contacts the wall 67, the stabilizer 66 may freely move relative to the cannula 68.

Figure 6:
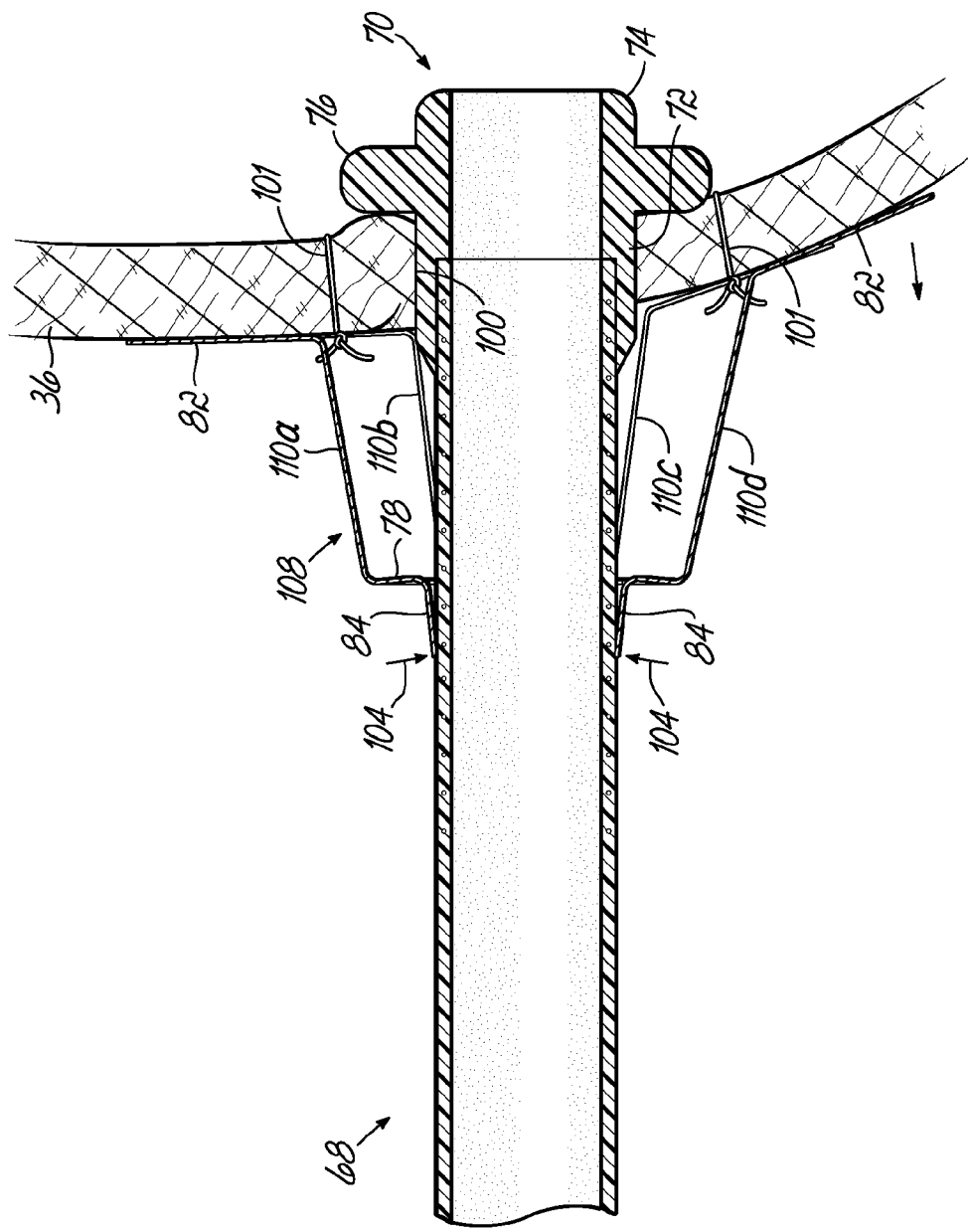
FIG. 6 is a side-elevational view, in cross-section, illustrating an alternate embodiment of a stabilizer for securing the position of the cannula to a vascular structure having an angled outer wall surface.

FIG. 6 illustrates an alternate embodiment of a stabilizer 108 that is configured to engage a vascular structure having an angled outer wall surface, which is illustrated as the wall of the aorta 36. Because the radius of curvature of the wall of the aorta 36, the outer surface curves away from at least one side of the incision 100 made for inserting the cannula 68. As a result, the stabilizer 108 may be constructed to include struts 110a-d having varying lengths. In this way, the stabilizer 108 is positioned such that the longer ones of the struts 110c, 110d will contact the outer surface of the aorta 36 having a greater degree of curvature directed away from the incision 100. As a result, the tip 70 of the cannula 68 may be stabilized in a position that is generally orthogonal to the wall of the aorta 36.

While movement of the stabilizer 66 may be accomplished by hand, it would be understood that a steering device (not shown) could engage the manipulation tabs 86 for advancing the stabilizer 66. The steering device could be a tube having an inner diameter that is sufficiently large to receive the cannula 68 and the arms 84 of the stabilizer 66. A distal surface of the tube could engage the manipulation tabs 86 such that a distally directed force applied to the tube is transferred via the manipulation tabs 86 to move the stabilizer 66 over the cannula 68.

With the cannula 68 positioned within the wall of the vascular structure and secured by the stabilizer 66, the proximal end of the cannula 68 may then be manipulated to the position of the circulatory assist device or as necessary according to the particular surgical procedure.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. An apparatus for stabilizing a cannula to a vascular structure, the apparatus comprising:
   (i) a ring adapted to circumferentially surround and be in slidable relation with the cannula;
   (ii) three or more struts coupled to the ring, each of the three or more struts having a distal end that extends distally and outwardly away from the ring by a first angle relative to a first axis that is parallel to a lengthwise central axis of the cannula;
   (iii) a contact pad coupled to and extending from the distal end of each of the three or more struts, wherein each contact pad extends away from the respective distal end by a second angle relative to the first axis, the second angle being greater than the first angle; and (iv) three or more arms coupled to the ring, each of the three or more arms extending proximally and inwardly away from the ring by a third angle relative to the first axis, wherein each of the three or more arms directly opposes a respective one of the three or more struts, wherein the contact pads, when engaging a wall of the vascular structure, are configured to radially outwardly deflect the three or more struts and radially inwardly deflect the three or more arms at an inward angle beyond the third angle to engage the arms into an outer wall of the cannula and thereby prevent axial movement of the apparatus relative to the cannula and thereby stabilize the cannula relative to the wall.

2. The apparatus of claim 1 further comprising:
three or more manipulation tabs radially extending from the ring, wherein each of the three or more manipulation tabs resides between successive ones of the three or more struts.

3. The apparatus of claim 2, wherein the width of each of the manipulation tabs ranges from about 0.5 mm (0.02 inches) to about 10 mm (0.4 inches).

4. The apparatus of claim 2 further comprising:
a strain relief groove between each manipulation tab and an adjacent one of the three or more struts.

5. The apparatus of claim 1, wherein the apparatus is constructed as a unitary structure.

6. The apparatus of claim 5, wherein the unitary structure is constructed from a superelastic material.

7. The apparatus of claim 5, wherein a material comprising the unitary structure ranges in thickness from about 0.10 mm (0.004 inches) to about 0.36 mm (0.014 inches).

8. The apparatus of claim 1, wherein a contour of each of the contact pads is circular, elliptical, or rectangular.

9. The apparatus of claim 8, wherein a perimeter of each of the contact pads is at least equal to a width of each of the three or more struts.

10. The apparatus of claim 1, wherein the first angle ranges from about 1 degree to about 15 degrees, the second angle ranges from about 75 degrees to about 89 degrees, and the third angle ranges from about 1 degree to about 25 degrees.

11. The apparatus of claim 1, wherein a length of each of the three or more struts ranges from about 1 mm (0.4 inches) to about 5 cm (1.97 inches).

12. The apparatus of claim 1, wherein a width of each of the three or more struts is selected such that a width-to-thickness ratio is greater than 2:1.

13. The apparatus of claim 1, wherein each of the contact pads includes a porous polymeric coating.

14. The apparatus of claim 1, wherein a length of each of the three arms is less than about ½ of a diameter of the ring.

15. A method of stabilizing a cannula to a vascular structure, the method comprising:

(i) inserting a distal end of the cannula through a wall of the vascular structure;

(ii) advancing a stabilizer over a length of the cannula to the wall of the vascular structure, the stabilizer comprising:

(a) a ring circumferentially surrounding and in slidable relation with the cannula;

(b) three or more struts coupled to the ring, each of the three or more struts having a distal end extending distally and outwardly from the ring by a first angle relative to a first axis that is parallel to a lengthwise central axis of the cannula;

(c) a contact pad coupled to and extending from the distal end of each of the three or more struts, wherein each contact pad extends away from the respective distal end by a second angle relative to the first axis, the second angle being greater than the first angle; and (d) three or more arms coupled to the ring, each of the three or more arms extending proximally and inwardly from the ring by a third angle relative to the first axis, wherein each of the three or more arms directly opposes a respective one of the three or more struts; and (iii) further advancing the stabilizer to the wall such that the contact pads engage the wall causing radially outward deflection of the three or more struts and radially inward deflection of the three or more arms beyond the third angle and into an outer wall of the cannula to thereby prevent axial movement of the stabilizer relative to the cannula and thereby stabilize the cannula relative to the wall.

16. The method according to claim 15 further comprising:
securing the cannula with purse string sutures before advancing the stabilizer.

17. An apparatus for stabilizing a cannula to a vascular structure, the apparatus comprising:
a ring adapted to circumferentially surround and be in slidable relation with the cannula;
three or more struts coupled to the ring, each of the three or more struts having a distal end that extends in a first direction away from the ring; and
three or more arms coupled to the ring, each of the three or more arms extending in a second direction away from the ring and generally opposing a respective one of the three or more struts, the second direction being different from the first direction,
wherein the three or more struts are configured to be deflected radially outwardly when the apparatus engages a wall of the vascular structure and to deflect the three or more arms radially inwardly to engage the arms into an outer wall of the cannula and thereby prevent axial movement of the apparatus relative to the cannula to stabilize the cannula relative to the wall.

18. The apparatus of claim 17 further comprising:
a contact pad coupled to the distal end of each of the three or more struts, the contact pads configured to engage the wall of the vascular structure and to deflect the three or more struts radially outwardly.

19. A cannula stabilization system comprising:
a cannula configured to extend through a wall of a vascular structure, the cannula having a lengthwise central axis;
a stabilizer configured to stabilize a position of the cannula relative to the wall, the stabilizer comprising:
a ring circumferentially surrounding and in slidable relation to the cannula;
three or more struts coupled to the ring, each of the three or more struts having a distal end that extends distally and outwardly away from the ring by a first angle relative to the lengthwise central axis;
a contact pad coupled to and extending from the distal end of each of the three or more struts, wherein each contact pads extends away from the respective distal end by a second angle relative to the lengthwise central axis, the second angle being greater than the first angle; and
three or more arms coupled to the ring, each of the three or more arms extending proximally and inwardly away from the ring by a third angle relative to the lengthwise central axis, wherein each of the three or more arms directly opposes a respective one of the three or more struts, wherein, when the cannula extends through the wall and the stabilizer slides over the cannula to engage the wall, the contact pads are configured to contact the wall, radially outwardly deflect the respective one of the three or more struts, radially inwardly deflect the respective one of the three or more arms at an inward angle beyond the third angle to engage the arms into an outer wall of the cannula and thereby prevent axial movement of the stabilizer relative to the cannula to stabilize the cannula relative to the wall.

* * * * *